United States Patent [19]

Raghunathan

[11] Patent Number: 4,517,179

[45] Date of Patent: May 14, 1985

[54] RAPID DISSOLVING, UNIFORM DRUG COMPOSITIONS AND THEIR PREPARATION

[75] Inventor: Yegnasawami Raghunathan, Fairport, N.Y.

[73] Assignee: Pennwalt Corporation, Philadelphia, Pa.

[21] Appl. No.: 586,605

[22] Filed: Mar. 6, 1984

Related U.S. Application Data

[63] Continuation-in-part of Ser. No. 490,056, Apr. 29, 1983, abandoned.

[51] Int. Cl.$^3$ .................... A61K 33/06; A61K 45/08
[52] U.S. Cl. .................................. 514/249; 514/781; 514/869; 514/960; 514/761; 514/951; 514/259
[58] Field of Search ................ 544/288; 424/154, 251, 424/35, 362

[56] References Cited

U.S. PATENT DOCUMENTS 3,134,719  5/1964  Sheth et al. .......................... 424/330
3,360,518  12/1967  Shetty .............................. 260/256.5
3,745,216  7/1973  Jen et al. ............................. 424/251

FOREIGN PATENT DOCUMENTS

WO81/02521  9/1981  PCT Int'l Appl. .
1177411  1/1970  United Kingdom .
1480188  7/1977  United Kingdom .
1573580  8/1980  United Kingdom .

OTHER PUBLICATIONS

Stauffer "DI-TAB" (1981), 18 pp., (Unmilled Dicalcium Phosphate in Direct Compression Tableting).
Burger, "Dissolution and Polymorphism of Metolazone", Drug Research 25:24–27 (1975).
Chiou et al., "Pharmaceutical Applications of Solid Dispersion Systems", Pharm. Sci. 60:1281–1302 (1971).
Lachman et al., "The Theory and Practice of Industrial Pharmacy", 2nd Ed., Lea & Febiger, pp. 328–337 (1976).
Navnit et al., "Influence of Dispersion Method on Dissolution Rate and Bioavailability of Digoxin from Triturations & Compressed Tablets II", Pharm. Sci. 63:3, 339–344 (1974).
Remington's Pharmaceutical Sciences, 15th Ed., Mack Publishng Company (1975).
Samyn et al., "Experiments in Powder Blending and Unblending", Pharm. Sci. 64:370–375 (1974).
Yamamoto et al., "Dissolution Behavior and Bioavailability of Phenyltoin from a Ground Mixture with Microcrystalline Cellulose", Pharm. Sci. 1484–1488.

*Primary Examiner*—Shep K. Rose

[57] ABSTRACT

Rapid dissolving uniform compositions of low water solubility drugs are formed from a dry mixture of the drug having a reduced particle size in combination with properly selected and sized excipients including microcrystalline cellulose, dibasic calcium phosphate, starches and a lubricant.

14 Claims, No Drawings

RAPID DISSOLVING, UNIFORM DRUG COMPOSITIONS AND THEIR PREPARATION

This application is a continuation-in-part of application Ser. No. 490,056, filed Apr. 29, 1983, and now abandoned.

BACKGROUND OF THE INVENTION

This invention relates generally to pharmaceutical preparations and more specifically to dosage preparations which provide rapid dissolution and increased bioavailability of drugs having low water solubility. The preparations also have good drug content uniformity.

Many useful drugs have water solubilities of about 1 part by weight per 100 parts by weight of water (10,000 mcg/ml) or less at 25° C. which can result in poor drug absorption and bioavailability. Many of these drugs are used in low doses (50 mg or less) and it is difficult to obtain good drug content uniformity especially in tablet dosage forms prepared by dry blending and direct compression.

The diuretic and antihypertensive agent metolazone is a sulfonamide derivative. Its chemical name is 2-methyl-3-o-tolyl-6-sulfamyl-7-chloro-1,2,3,4-tetrahydro-4-quinazolinone, and it is described in U.S. Pat. No. 3,360,518 which is incorporated by reference. Metolazone has a water solubility of approximately 60.3 mcg/ml at 25° C. and 100.0 mcg/ml at 36° C. A problem associated with dosage forms of metolazone is its poor dissolution characteristics, which is caused by poor water solubility. Burger et al., *Drug Research*, 25, 24 (1975) reported the intrinsic solution rate of five different solid forms of metolazone in n-butanol, water and 0.01N hydrochloric acid. The amorphous and metastable metolazone of softening temperature 140°–155° C. was observed to dissolve about 8 times faster than in 0.01N hydrochloric acid than the stable modification (mp. 267°–270° C.). On account of the metastable nature of the more soluble polymorphic forms, as well as the inconsistency with their manufacture, they are unsuitable for practical use. Accordingly, dosage forms of stable metolazone and other drugs of low water solubility having improved dissolution characteristics, good drug uniformity, and which are easily manufactured are desired because they would be expected to make the drug more bioavailable. Better bioavailability could permit a smaller dosage of drug to be used and consequently reduce side effects such as hypokalemia or abnormally low potassium levels in the blood which result from metolazone usage. I have now discovered dosage forms of poorly absorbed drugs which provide a dramatic increase in dissolution rates and which can be readily manufactured to provide good drug uniformity especially in dosages containing less than 50 mg of the drug.

The improved result is obtained by using certain excipient mixtures and providing the drug in the form of fine particles.

BRIEF SUMMARY OF THE INVENTION

In accordance with this invention there is provided a rapid dissolving dosage form of a low solubility drug prepared from a dry mixture comprising the drug, having a particle size distribution such that the major portion of drug particles are less than about 155 μm in diameter and preferably less than about 100 μm, microcrystalline cellulose and starch. When the dosage form is compressed tablets, unmilled or coarse milled calcium phosphate and a lubricant are added to the mixture.

Also provided is a process for forming rapid dissolving tablets containing a low solubility drug comprising fine milling the drug, mixing the drug with starch, microcrystalline cellulose, unmilled or coarse milled dibasic calcium phosphate, and a lubricant so as to form a uniform, free-flowing, dry mixture and then compressing the mixture to form tablets.

DETAILED DESCRIPTION

The invention can improve the dissolution characteristics of drugs having low water solubilities especially those which are either slightly soluble(SS) (1 part by wt in 100 to 1000 parts by wt of water at 25° C.), very slightly soluble (VSS) (1 part by weight in 1000 to 10,000 parts by wt of water at 25° C.), or practically insoluble (PI) (less than 1 part by weight in 10,000 parts by wt. of water at 25° C.). These drugs are referred to in the specification and claims as being "low solubility drugs".

Many diuretics have solubilities of 1 part by wt or less in 100 parts by wt of water at 25° C. as listed below:

| SS | VSS | PI |
|---|---|---|
| amiloride | ethacrynate | bendrofluazide |
| bumetamide | methylclothiazide | benzthiazide |
| butathiazide | methazolamide | chlorthalidone |
| canrenone | quinethazone | cyclothiazide |
| clopamide | triamterene | epithiazide |
|  | trichloromethiazide | furosemide |
|  | hydroflumethiazide | hydrochlorthiazide |
|  |  | mebutizide |
|  |  | metolazone |
|  |  | paraflutizide |
|  |  | polythiazide |
|  |  | xipamide |

Other drugs which have low water solubilities include, for example, methaqualone, ergotamine tartrate, chloropromazine, atropine, codeine, norethindrone acetate, phenobarbital, indomethacin, doxepin, acetohexamide, cyclizine, cyclizine hydrochlorde, diazepam, reserpine, acetyldigitoxin, betamethasone, bisacodyl, cephaloglycin, chloramphenicol, chlorotrianisene, erythromycin estolate, griseofulvin, oxazepam, quinidine sulfate, cortisone acetate, digitoxin, disulfiram, erythromycin, estradiol, methylprednisolone, paramethasone acetate, pargyline hydrochloride, prednisolone, primidone, simethicone, sulfisoxazole, testolactone, and testosterone.

Many of the drugs listed above are generally used in dosages of 50 mg or less. The increased dissolution rates of the compositions of the invention can permit even smaller dosages per tablet or capsule. As the amount of drug per dose is decreased, drug content uniformity becomes more difficult to achieve. The compositions of the invention have been found to provide improved dosage uniformity even with drug contents of less than 1 mg.

The high melting (267°–270° C.), stable, monocrystalline form of metolazone as prepared by the process described in U.S. Pat. No. 3,360,518 typically has a particle size distribution as follows:

| $d_{16\%}$ | $d_{50\%}$ | $d_{84\%}$ | $\sigma g$ |
|---|---|---|---|
| 460 μm | 190 μm | 83 μm | 2.5 | where d is the particle diameter in μm at the indicated percentage by weight and $\sigma g$ is the geometric standard deviation.

The water solubility of the monocrystalline metolazone at 25° C. is about 60 mcg/ml. In order to provide improved dissolution and good drug uniformity in a compressed tablet or capsule dosage form, the metolazone or other drug is fine milled, for example, in a communicating mill such as a Fitzpatrick mill fitted with a #1 screen (equivalent screen) opening of 0.033 inch) or a Mikropulverizer fitted with a #3460 herring bone screen (equivalent screen opening of 0.013 inch). The latter gives smaller size particles which are preferred (84% by weight less than about 100 μm). The amount of metolazone or other drug per dose generally ranges from about 0.05 to 10 wt percent.

The excipients are selected to be compatible with the drug and provide a formulation mixture which has good flow to the tableting machine when tablets are desired while avoiding any unmixing tendencies which would result in inconsistent drug content between tablets. The excipients are also selected to provide enhanced dissolution properties to the drug and, therefore, better drug availability.

The excipients include but are not limited to microcrystalline cellulose and dibasic calcium phosphate as diluents. Microcrystalline cellulose also acts as a filler and disintegrant.

The particle size distribution (diameter d and geometric standard deviation $\sigma g$) of a typical commercially available cellulose material is as follows:

| $d_{16\%}$ | $d_{50\%}$ | $d_{84\%}$ | $\sigma g$ |
|---|---|---|---|
| 77 μm | 44 μm | 25 μm | 1.74 |

The amount of microcrystalline cellulose in the composition ranges from about 10 to 90 wt percent and preferably from about 40 to 50 wt percent.

Dibasic calcium phosphate is used to improve the flow of the formulation mixture to permit direct compression of the mixture into tablets. The particle size distribution of a typical commercially available unmilled calcium phosphate material is as follows:

| $d_{16\%}$ | $d_{50\%}$ | $d_{84\%}$ | $\sigma g$ |
|---|---|---|---|
| 225 μm | 140 μm | 88 μm | 1.63 |

I have found that coarse milling the calcium phosphate improved the consistency of the drug concentration in the compressed tablets. The coarse milling is believed to overcome an unmixing tendency which has been noted in other systems when using a flow-enhancing excipient. A typical particle size range distribution resulting from coarse milling through a Fitzpatrick comminuting mill fitted with a #000 screen (equivalent to a 0.020 inch opening) at fast speed with impact forward is as follows:

| $d_{16\%}$ | $d_{50\%}$ | $d_{84\%}$ | $\sigma g$ |
|---|---|---|---|
| 170 μm | 98 μm | 44 μm | 1.33 |

The amount of dibasic calcium phosphate in the composition ranges from 10 to 90 wt percent and preferably 35 to 50 wt percent.

Starches are added to the formulation mixture to improve the disintegration and dissolution of the composition. A fatty acid or fatty acid salt, for example, magnesium stearate, is added as a lubricant or improve the flow of the formulation mixture in manufacture.

The amount of starch in the composition typically ranges from about 1 to 20 wt percent and the amount of lubricant from about 0.1 to 3.0 wt percent.

Dyes can be added for identification purposes.

A typical tablet weight ranges from 50 to 400 mg.

The invention is further illustrated by, but is not intended to be limited to, the following examples in which the materials and tablets were evaluated using the methods described below:

Particle Size Distribution:

The particle size distributions of drugs and excipients were determined by a screen analysis technique. A 5 gm sample of each test material was placed on the top screen of a set of six US standard screens of an Allen Bradley Sonic Sifter. The screens were pulsed for 15 minutes. The following screens were used: 80 mesh (180 μm), 100 mesh (150 μm), 140 mesh (106 μm), 200 mesh (75 μm), 270 mesh (53 μm) and 400 mesh (38 μm). The weights of the fractions retained on the screens were obtained. Particle sizes (d) at specific weight percents (16, 50, and 84) were obtained from a log probability plot of the data as described by Edmundson (*Advances in Pharmaceutical Sciences*, Bean, H.S. et al. Editors, Academic, London, England p. 95, 1967). These particle sizes are described as $d_{16}$, $d_{50}$, and $d_{84}$.

The slopes of the lines from the plots were calculated to give the geometric standard deviation ($\sigma g$).

Tablet Weight:

At least 10 tablets were weighed individually. The average and standard deviation of the tablet weights were then calculated from these values.

Tablet Thickness:

The thickness values of at least 10 tablets were measured with an Ames thickness gage. The average of these values were then calculated.

Hardness:

The hardness values of at least 10 tablets were obtained with a Pfizer hardness tester. The average and standard deviation of these values were then calculated.

Friability:

Ten tablets were weighed before and after being placed in a Roche friabilator for 10 minutes. The difference in weight between the two weighings was expressed as % friability.

Disintegration:

Six tablets were placed in a USP disintegration apparatus (U.S. Pharmacopia, revision XX, page 958) immersed in purified water (USP) at 37° C. The time necessary for all tablets to pass through the screens of the basket apparatus was reported.

Content Uniformity Assay for Drug:

Ten tablets were assayed individually for drug content by an HPLC method. These values were then expressed as % of theoretical content of the tablets. Averages and standard deviations of these values were obtained.

Dissolution Procedure for Tablets:

Th dissolution assembly was essentially the same as described in the USP XX, page 959 under Apparatus 1. The following details the equipment and conditions of the dissolution:

1000 ml of Hydrochloric acid solution (0.1N), was placed in a one liter vessel (Kimble glass number 33700, 16 cm high, 10 cm inside diameter). The dissolution medium was maintained at 37° C.±0.5° C. by immersing the vessel in a suitable water bath. Six such vessels were set up. The dissolution media in the six vessels were stirred with type 316 stainless steel basket type stirrers at 50 rpm driven by a Hanson multiple spindle drive. Each of the basket stirrers contained one tablet. The baskets were all simultaneously lowered into the dissolution media at the start of the dissolution. Filtering devices with small cotton plugs enabled the dissolution media to filter into glass tubes from which they were pumped through polyethylene tubes into 1 cm path flow through cells and returned to the dissolution vessels. A Master Flex pump drive was used for this purpose. A flow rate of approximately 16 ml/min. was maintained in each of the cells.

A Beckman Model 25 or 35 spectrophotometer with a multiple channel chart recorder was used to monitor the change in absorbance of the samples at 235 nm for metolazone (310 nm for triamterene) as a function of time. Metolazone (or triamterene) standards were run similarly and sample concentrations calculated therefrom.

EXAMPLE 1

Metolazone Tablets 2.5 mg

One hundred and fifty thousand tablets of the following composition were prepared. A direct compression method was used to compound the tablets.

|  | Input/Tablet | Input/150,000 Tablets |
| --- | --- | --- |
| Metolazone, moncrystalline | 2.50 mg | 375.00 g |
| Microcrystalline cellulose (Avicel PH101) | 59.30 mg | 8,895.00 g |
| Unmilled calcium phosphate, dibasic | 48.70 mg | 7,305.00 g |
| Starch 1500 (pregelatinized starch NF) | 13.00 mg | 1,950.00 g |
| Modified starch (Explotab, E. Mendell) | 5.20 mg | 780.00 g |
| Magnesium stearate | 1.30 mg | 195.00 g |
| Total | 130.00 mg | 19,500.00 g |

Procedure:

1. The modified starch and starch 1500 were passed through a #30 mesh stainless steel screen.

2. The two starches from Step 1 above were mixed in a "double cone" blender for 10 minutes. The metolazone was passed through a #3460 H.B. screen fitted on a Mikropulverizer. (#3460 H.B. screen is equivalent to 0.013 inch opening.)

3. A geometric dilution of the milled metolazone was then made into the modified starch/starch 1500 mix from Step 2.

4. The unmilled calcium phosphate was passed through a "Fitzmill" fitted with a 000 screen (000 screen is equivalent to 0.020 inch opening) and run at high speed with impact forward.

5. The microcrystalline cellulose and the milled calcium phosphate from step 4 were then mixed for 5 minutes in a suitable size Lodige mixer.

6. The geometric dilution from Step 3 was added to Step 5 and mixed for 15 additional minutes.

7. The magnesium stearate was passed through a #30 mesh stainless steel screen and mixed with a small portion of the blend from step 6. This was then added to the blend and mixed for 1½ minutes.

8. 130 mg tablets were compressed using ¼" standard concave tooling.

The following data were obtained on these tablets.

| Tablet Weight: 130.1 ± 2.1 mg | Dissolution (wt % metolazone released - 50 rpm, 1000 ml 0.1N HCL, USP basket): | | | |
| --- | --- | --- | --- | --- |
| Tablet Thickness: 0.144 ± 0.6 in. | | | | |
| Hardness: 10.8 ± 0.8 kg | | | | |
| Friability: 0.6% | 0.5 hr | 1 hr | 2 hr | 3 hr |
| Disintegration: 15 seconds | 40.7 | 51.6 | 64.0 | 72.0 |
| Drug Content Uniformity assay: 97.0 ± 4.0% | | | | |

The particle size distribution of the milled metolazone was as follows:

| $d_{16\%}$ | $d_{50\%}$ | $d_{84\%}$ | $\sigma g$ |
| --- | --- | --- | --- |
| 94 μm | 56 μm | 34 μm | 1.73 |

EXAMPLE 2

Metolazone Tablet 1.0 mg

Five thousand tablets of the following composition were prepared. A direct compression method was used to compound the tablets.

|  | Input/Tablet | Input/5.000 Tablets |
| --- | --- | --- |
| Metolazone, monocrystalline | 1.00 mg | 5.00 g |
| Microcrystalline cellulose (Avicel PH101) | 191.00 mg | 955.00 g |
| Unmilled calcium phosphate, dibasic | 148.00 mg | 740.00 g |
| Starch 1500 (pregelatinized starch NF) | 40.00 mg | 200.00 g |
| Modified starch (Explotab, E. Mendell) | 16.00 mg | 80.00 g |
| Magnesium stearate | 4.00 mg | 20.00 g |
| Total | 400.00 mg | 2,000.00 g |

Procedure

1. The modified starch and starch 1500 were passed through a #30 mesh stainless steel screen.

2. The two starches from Step 1 were mixed in a "double cone" blender for 10 minutes.

3. The metolazone was passed through a #3460 H.B. screen fitted on a Mikropulverizer. (#3460 H.B. screen is equivalent to 0.013 inch opening.) The particle size distribution was as described in Example 1.

4. A geometric dilution of the milled metolazone was then made into the modified starch/starch 1500 mix from Step 2.

5. The microcrystalline cellulose and the unmilled calcium phosphate were mixed for 5 minutes in a suitable "double cone" mixer.

6. The geometric dilution from Step 4 was added to Step 5 and mixed for 15 additional minutes.

7. The magnesium stearate was passed through a #30 mesh stainless steel screen and mixed with a small portion of the blend from Step 6. This was then added to the blend and mixed for 1½ minutes.

8. 400 mg tablets were compressed using ⅜" flat faced beveled edged tooling.

The following data were obtained on these tablets:

| Tablet Weight: 398.9 ± 2.0 mg | Dissolution (wt % metolazone released - 50 rpm, 1000 ml 0.1N HCL, USP basket): | | | |
|---|---|---|---|---|
| Tablet Thickness: 0173 in. | | | | |
| Hardness: 11.3 ± 0.6 kg | | | | |
| Friability: 0.28% | 0.5 hr | 1 hr | 2 hr | 3 hr |
| Disintegration: 15 seconds | 51.5 | 63.9 | 75.9 | 82.2 |
| Drug Content Uniformity assay: 97.1 ± 3.2% | | | | |

EXAMPLE 3

Metolazone Tablets 1.0 mg

Five thousand tablets of the following composition were prepared. A direct compression method was used to compound the tablets.

| | Input/Tablet | Input/5,000 Tablets |
|---|---|---|
| Metolazone, Monocrystalline, | 1.00 mg | 5.00 g |
| Microcrystalline cellulose (Avicel PH101) | 191.00 mg | 955.00 g |
| Unmilled calcium phosphate, dibasic | 148.00 mg | 740.00 g |
| Starch 1500 (pregelatinized starch NF) | 40.00 mg | 200.00 g |
| Modified starch (Explotab, E. Mendell) | 16.00 mg | 80.00 g |
| Magnesium stearate | 4.00 mg | 20.00 g |
| Total | 400.00 mg | 2000.00 g |

Procedure

1. The modified starch and starch 1500 were passed through a #30 mesh stainless steel screen.
2. The two starches from Step 1 were mixed in a "double cone" blender for 10 minutes.
3. The metolazone was passed through a "Fitzmill" fitted with a #1 screen (#1 screen is equivalent to 0.033 inch opening) and run at high speed with impact forward.
4. A geometric dilution of the milled metolazone was then made into the modified starch/starch 1500 mix from Step 2.
5. The microcrystalline cellulose and the unmilled calcium phosphate were mixed for 5 minutes in a suitable "double cone" mixer.
6. The geometric dilution from Step 4 was added to Step 5 and mixed for 15 additional minutes.
7. The magnesium stearate was passed through a #30 mesh stainless steel screen and mixed with a small portion of the blend from Step 6. This was then added to the blend and mixed for 1½ minutes.
8. 400 mg tablets were compressed using ⅜" flat faced beveled edged tooling.

The following data were obtained on these tablets:

| Tablet Weight: 396.4 ± 1.6 mg | Dissolution (wt % metolazone released - 50 rpm, 1000 ml 0.1N HCL, USP basket): | | | |
|---|---|---|---|---|
| Tablet Thickness: 0.172 in. | | | | |
| Hardness: 12.2 ± 0.6 kg | | | | |
| Friability: 0.15% | 0.5 hr | 1 hr | 2 hr | 3 hr |
| Disintegration: 10 seconds | 43.8 | 56.5 | 71.6 | 81.5 |
| Drug Content Uniformity assay: 97.5 ± 4.4% | | | | |

The slightly lower dissolution rate and higher drug content uniformity variation when compared to Example 2 indicate that very fine milling of the metolazone is preferred. The particle size distribution of the fine-milled metolazone was as follows:

| $d_{16\%}$ | $d_{50\%}$ | $d_{84\%}$ | $\sigma g$ |
|---|---|---|---|
| 155 μm | 86 μm | 48 μm | 1.9 |

EXAMPLE 4

Metolazone Tablets 0.5 mg

Five thousand tablets of the following composition were prepared. A direct compression method was used to compound the tablets.

| | Input/Tablet | Input/5,000 Tablets |
|---|---|---|
| Metolazone, monocrystalline | 0.50 mg | 2.50 g |
| Microcrystalline cellulose (Avicel PH101) | 191.00 mg | 955.00 g |
| Unmilled calcium phosphate, dibasic | 148.50 mg | 742.50 g |
| Starch 1500 (pregelatinized starch NF) | 40.00 mg | 200.00 g |
| Modified starch (Explotab, E. Mendell) | 16.00 mg | 80.00 g |
| Magnesium stearate | 4.00 mg | 20.00 g |
| Total | 400.00 mg | 2,000.00 g |

Procedure

1. The modified starch and starch 1500 were passed through a #30 mesh stainless steel screen.
2. The two starches from Step 1 were mixed in a "double cone" blender for 10 minutes.
3. The metolazone was passed through a #3460 H.B. screen fitted on a Mikropulverizer. (#3460 H.B. screen is equivalent to 0.013 inch opening.) The particle size distribution was as described in Example 1.
4. A geometric dilution of the milled metolazone was then made into the modified starch/starch 1500 mix from Step 2.
5. The unmilled calcium phosphate was passed through a "Fitzmill" fitted with a 000 screen (000 screen is equivalent to 0.020 inch opening) and run at high speed with impact forward.
6. The microcrystalline cellulose and the milled calcium phosphate from Step 5 were then mixed for 5 minutes in a suitable "double cone" mixer.
7. The geometric dilution from Step 4 was added to Step 6 and mixed for 15 additional minutes.
8. The magnesium stearate was passed through a #30 mesh stainless steel screen and mixed with a small portion of the blend from Step 7. This was then added to the blend and mixed for 1½ minutes.
9. 400 mg tablets were compressed using ⅜" flat faced beveled edged tooling.

The following data were obtained on these tablets:

| Tablet Weight: 399.0 ± 2.7 mg | Dissolution (wt % metolazone released - 50 rpm, 1000 ml 0.1n HCL, USP basket): | | | | |
|---|---|---|---|---|---|
| Tablet Thickness: 0.714 in. | | | | | |
| Hardness: 11.4 ± 0.7 kg | 0.25 hr | 0.5 hr | 1 hr | 2 hr | 3 hr |
| Friability: 0.4% | 45.6 | 58.9 | 70.3 | 79.0 | 82.7 |
| Disintegration: 15 seconds | | | | | |
| Drug Content Uniformity assay: 104.6 ± 2.5% | | | | | |

When the process of Example 4 was followed without milling either the metolazone or the calcium phosphate the following data on the so-manufactured tablets were obtained:

| Tablet Weight: 397.8 ± 4.3 mg  Tablet Thickness: 0.173 in.  Hardness: 11.0 ± 1.4 kg  Friability: 0.28%  Disintegration: 10 seconds  Drug Content Uniformity assay: 106.7 ± 18.5% | Dissolution (wt % metolazone released - 50 rpm, 1000 ml 0.1N HCL, USP basket): | | | | |
|---|---|---|---|---|---|
| | 0.25 hr | 0.5 hr | 1 hr | 2 hr | 3 hr |
| | 13.0 | 19.7 | 29.3 | 38.9 | 45.3 |

The low dissolution rate and poor uniformity assay results make these tablets unacceptable.

When the metolazone was micropulverized as in Step 3 of Example 4 the acceptability of the resulting tablet was improved with the drug content assay being 94.5±6 and the metolazone dissolution from the tablets was 68.0% in one hour.

When all the calcium phosphate was replaced with microcrystalline cellulose (400 mg tablets), flow problems occurred and hard tablets resulted. In another trial with 310 mg tablets, flow and dissolution were satisfactory but the drug content assay was 108±6.0%. Leaving out both calcium phosphate and starch resulted in poor dissolution of metolazone (36.8% in one hour).

EXAMPLE 5

Metolazone Tablets 0.5 mg

Ten thousand tablets of the following composition were prepared. A direct compression method was used to compound the tablets.

| | Input/Tablet | Input/10,000 Tablets |
|---|---|---|
| Metolazone, monocrystalline | 0.50 mg | 5.00 g |
| Microcrystalline cellulose (Avicel PH101) | 72.00 mg | 720.00 g |
| Unmilled calcium phosphate, dibasic | 55.00 mg | 550.00 g |
| Starch 1500 (pregelatinized starch NF) | 15.00 mg | 150.00 g |
| Modified starch (Explotab, E. Mendell) | 6.00 mg | 60.00 g |
| Magnesium stearate | 1.50 mg | 15.00 g |
| Total | 150.00 mg | 1,500.00 g |

Procedure

1. The modified starch and starch 1500 were passed through a #30 mesh stainless steel screen.
2. The two starches from Step 1 were mixed in a "double cone" blender for 10 minutes.
3. The metolazone was passed through a #3460 H.B. screen fitted on a Mikropulverizer. (#3460 H.B. screen is equivalent to 0.013 inch opening.)
4. A geometric dilution of the milled metolazone was then made into the modified starch/starch 1500 mix from Step 2 above.
5. The unmilled calcium phosphate was passed through a "Fitzmill" fitted with a 000 screen (000 screen is equivalent to 0.020 inch opening) and run at high speed with impact forward.
6. The microcrystalline cellulose and the milled calcium phosphate from Step 5 were then mixed for 5 minutes in a suitable "double cone" mixer.
7. The geometric dilution from Step 4 was added to Step 6 and mixed for 15 additional minutes.
8. The magnesium stearate was passed through a #30 mesh stainless steel screen and mixed with a small portion of the blend from Step 7. This was added to the blend and mixed for 1½ minutes.
9. 150 mg tablets were compressed using ¼" standard concave tooling.

The following data were obtained on these tablets:

| Tablet Weight: 150.9 ± 4.2 mg  Tablet Thickness: 0.162 in.  Hardness: 9.9 ± 1.4 kg  Friability: 0.0%  Disintegration: 15 seconds  Drug Content Uniformity assay: 105.9 ± 3.5% | Dissolution (wt % metolazone released - 50 rpm, 1000 ml 0.1N HCL, USP basket): | | | | |
|---|---|---|---|---|---|
| | 0.25 hr | 0.5 hr | 1 hr | 2 hr | 3 hr |
| | 44.4 | 57.4 | 66.8 | 76.7 | 81.3 |

EXAMPLE 6

Example 5 was repeated using the following formulation with batch sizes of 10,000 and 150,000 130 mg tablets:

| | Input/Tablet | Input/10,000 Tablets |
|---|---|---|
| Metolazone, monocrystalline | 0.50 mg | 5.00 g |
| Microcrystalline cellulose (Avicel PH101) | 61.30 mg | 613.00 g |
| Unmilled calcium phosphate, dibasic | 48.70 mg | 487.00 g |
| Starch 1500 (pregelatinized starch NF) | 13.00 mg | 130.00 g |
| Modified starch (Explotab, E. Mendell) | 5.20 mg | 52.00 g |
| Magnesium stearate | 1.30 mg | 13.00 g |
| Total | 130.00 mg | 1,300.00 g |

For the 10,000 tablet batch, the tablet weight variation was 130±1.4 mg the drug content uniformity was 97.4±1.8% and the metolazone dissolution at the end of one hour was 70.2%.

For the 150,000 tablet batch, the tablet weight variation was 129±1.9 mg the drug content uniformly was 105±3.5 and the metolazone dissolution at the end of one hour was 73.4%.

EXAMPLE 7

Metolazone Tablets 0.25 mg

Fifty thousand tablets of the following composition were prepared. A direct compression method was used to compound the tablets.

| | Input/Tablet | Input/50,000 Tablets |
|---|---|---|
| Metolazone, monocrystalline | 0.25 mg | 12.5 g |
| Microcrystalline cellulose (Avicel PH101) | 191.00 mg | 9,550.00 g |
| Unmilled calcium phosphate, dibasic | 148.75 mg | 7,437.50 g |
| Starch 1500 (pregelatinized starch NF) | 40.00 mg | 2,000.00 g |
| Modified starch (Explotab, E. Mendell) | 16.00 mg | 800.00 g |
| Magnesium stearate | 4.00 mg | 200.00 g |
| Total | 400.00 mg | 20,000.00 g |

Procedure

1. The modified starch and starch 1500 were passed through a #30 mesh stainless steel screen.
2. The two starches from Step 1 were mixed in a "double cone" blender for 10 minutes.

3. The metolazone was passed through a #3460 H.B. screen fitted on a Mikropulverizer. (#3460 H.B. screen is equivalent to 0.013 inch opening.) The particle size distribution was as described in Example 1.

4. A geometric dilution of the milled metolazone was then made into the modified starch/starch 1500 mix from Step 2.

5. The unmilled calcium phosphate was passed through a "Fitzmill" fitted with a 000 screen (000 screen is equivalent to 0.020 inch opening) and run at high speed with impact forward.

6. The microcrystalline cellulose and the milled calcium phosphate from Step 5 were mixed for 5 minutes in a suitable Lodige mixer.

7. The geometric dilution from Step 4 was added to Step 6 and mixed for 15 additional minutes.

8. The magnesium stearate was passed through a #30 mesh stainless steel screen and mixed with a small portion of the blend from Step 6. This was then added to the blend and mixed for 1½ minutes.

9. 400 mg tablets were compressed ⅜″ flat faced beveled edged tooling.

The following data were obtained on these tablets:

| Tablet Weight: 398.9 ± 3.5 mg | Dissolution (wt % metolazone released - 50 rpm, 1000 ml 0.1N HCL, USP basket): | | | |
|---|---|---|---|---|
| Tablet Thickness: 0.172 in. | | | | |
| Hardness: 9.8 ± 0.6 kg | | | | |
| Friability: 0.55% | 0.5 hr | 1 hr | 2 hr | 3 hr |
| Disintegration: 15 seconds | 72.6 | 83.9 | 95.3 | 98.2 |
| Drug Content Uniformity assay: 96.8 ± 3.0% | | | | |

As illustrated by the foregoing examples, a uniform, free-flowing and directly compressible formulation of metolazone is obtained by the inclusion of a combination of microcrystalline cellulose and coarsely milled calcium phosphate in the formula. Either of the two excipients alone do not produce the required properties of good flow, rapid dissolution and drug uniformity. Coarse milling of the calcium phosphate increased the consistency of metolazone concentration in the tablets.

EXAMPLE 8

Triamterene Tablets 50 mg

Twenty-thousand tablets of the following composition were prepared, a direct compression method was used to compound the tablets.

| | Input/Tablet | Input/20,000 Tablets |
|---|---|---|
| Triamterene | 50.00 mg | 1000 g |
| Microcrystalline Cellulose | 147.50 mg | 2950 g |
| Unmilled Calcium phosphate dibasic | 144.50 mg | 2890 g |
| Starch 1500 (pregelatinized) starch NF) | 40.00 mg | 800 g |
| Modified Starch | 16.00 mg | 320 g |
| Magnesium Stearate | 2.00 mg | 40 g |
| Total | 400.00 mg | 8000 g |

The triamterene had a particle size of

| d 16% | d 50% | d 84% |
|---|---|---|
| 76μm | 41μm | 17μm |

Procedure

1. The microcrystalline cellulose and unmilled dibasic calcium phosphate were mixed for 5 minutes in a suitable blender.

2. The triamterene and 1000 grams of the mixture from step 1 were mixed for 5 minutes in a suitable blender, another 2000 grams of the mixture were then added with mixing for 5 minutes and then the final portion of the mixture from step 1 was added and mixed for 5 minutes.

3. The starches were mixed for 5 minutes.

4. The mixture from step 2 was added in three increments (1500 gms 2500 gms, remainder) to the starch mixture with 5 minutes mixing after each addition.

5. The magnesium stearate was passed through a #30 mesh stainless steel screen, added to the mixture from step 4 and mixed for two minutes.

6. 400 mg tablets were compressed using ⅜″ flat faced beveled edged tooling.

The following data were obtained on these tablets:

| Tablet Weight: 403.6 mg | Dissolution (wt % triamterene released 50 rpm, 1000 ml 0.1N HCl, USP basket): | | |
|---|---|---|---|
| Tablet Thickness: 0.186 in. | | | |
| Hardness: 4.8 Kg | | | |
| Disintegration: 22.5 seconds | 0.5 hr. | 1 hr. | 3 hr. |
| Drug Content Uniformity assay; 90.2 ± 3.2% | 28.3 | 44.5 | 76.0 |

The foregoing invention provides rapid dissolving drug compositions of different sizes and dosages which are readily manufactured into tablets by direct compression to consistently uniform drug contents (less than ±4% variation). Rapid dissolving capsule dosage forms can also be prepared. The results are achieved by the particular combination of excipients and fine milling of the drugs when necessary so that the drugs are provided in the form of fine particles.

Fine particle size was found essential to the rapid dissolution of the drug and the uniformity of the drug dosage.

I claim:

1. A rapid dissolving pharmaceutical composition prepared from a dry mixture comprising from about 0.05 to 12.5 weight percent of a low solubility drug having a particle size distribution such that the major portion by weight of the particles are less than about 155 μm in diameter, from about 10 to 90 weight percent of microcrystalline cellulose, from about 10 to 90 weight percent of unmilled or coarse milled dibasic calcium phosphate, from about 0.1 to 3.0 percent of lubricant, and from about 1 to 20 weight percent of starch.

2. The composition of claim 1 wherein the drug is metolazone.

3. The composition of claim 1 wherein the lubricant is a fatty acid or a fatty acid salt.

4. The composition of claim 3 wherein 84 percent by weight of the drug particles are less than about 100 μm in diameter.

5. The composition of claim 1 wherein the amount of microcrystalline cellulose ranges from about 40 to 50 weight percent and the amount of dibasic calcium phosphate ranges from about 35 to 50 weight percent.

6. The composition of claim 5 wherein the tablet contains from about 0.25 to 50 mg of drug.

7. The composition of claim 5 wherein the tablet contains from about 0.25 to 2.5 mg. of metolazone.

8. The composition of claim 1 wherein the mixture contains coarse milled dibasic calcium phosphate wherein 50 percent by weight of the dibasic calcium phosphate particles have a diameter of less than about 100 μm.

9. A process for forming rapid dissolving pharmaceutical compositions containing a low solubility drug comprising mixing the drug with microcrystalline cellulose, starch, unmilled or coarse milled dibasic calcium phosphate, and a lubricant so as to form a uniform, free flowing, dry mixture comprising from about 0.05 to 12.5 weight percent of drug having a particle size distribution such that the major portion by weight of the particles are less than about 155 μm in diameter, from about 10 to 90 weight percent microcrystalline cellulose, from about 1 to 20 weight percent starch, from about 10 to 90 weight percent unmilled or coarse milled dibasic calcium phosphate and from about 0.1 to 3.0 weight percent of lubricant and then compressing the mixture to form tablets or filling the mixture into capsules.

10. The process of claim 9 including the step of fine milling the drug prior to mixing.

11. The composition of claim 1 in the form of a compressed tablet.

12. The composition of claim 1 wherein the drug is triamterene.

13. The composition of claim 1 wherein the drug has a particle size distribution such that the major portion by weight of the particles are less than about 100 μm in diameter.

14. The composition of claim 1 wherein the drug has a water solubility at a temperature of about 25° C. of about 1 part by weight or less in 100 parts by weight of water.

* * * * *

UNITED STATES PATENT AND TRADEMARK OFFICE
CERTIFICATE OF CORRECTION

PATENT NO. : 4,517,179
DATED : May 14, 1985
INVENTOR(S) : Yegnasawami Raghunathan It is certified that error appears in the above-identified patent and that said Letters Patent are hereby corrected as shown below:

Column 12, line 55 as reads "3" should read --13--.

Column 12, lines 62 and 64 as read "5" should read -- 11 --.

Signed and Sealed this

Seventeenth Day of September 1985

[SEAL]

Attest:

Attesting Officer

DONALD J. QUIGG

Commissioner of Patents and Trademarks—Designate